United States Patent [19]
Richie

[11] Patent Number: 5,626,738
[45] Date of Patent: May 6, 1997

[54] METHODS FOR THE SEPARATION AND DETECTION OF NITROSOTHIOLS

[75] Inventor: John P. Richie, Yorktown Hts., N.Y.

[73] Assignee: American Health Foundation, Valhalla, N.Y.

[21] Appl. No.: 560,341

[22] Filed: Nov. 17, 1995

[51] Int. Cl.$^6$ .................................................. G01N 27/26
[52] U.S. Cl. ........................... 205/444; 204/400; 204/409; 205/780.5; 205/786.5; 205/787
[58] Field of Search ........................ 205/444, 780.5, 205/486.5, 787

[56] References Cited

U.S. PATENT DOCUMENTS

| | | | |
|---|---|---|---|
| 3,594,294 | 7/1971 | Pretorius et al. | 205/787 |
| 3,778,230 | 12/1973 | Arikawa | 23/230 |
| 4,071,405 | 1/1978 | Soda | 195/29 |
| 4,072,584 | 2/1978 | Cipris et al. | 205/444 |
| 4,330,298 | 5/1982 | Hawn et al. | 205/786.5 |
| 4,404,065 | 9/1983 | Matson | 204/1 T |
| 4,413,505 | 11/1983 | Matson | 73/61.1 |
| 4,511,659 | 4/1985 | Matson | 436/150 |
| 4,554,064 | 11/1985 | McClintock | 204/411 |
| 4,705,620 | 11/1987 | Bricker et al. | 205/444 |
| 4,863,873 | 9/1989 | Matson | 436/63 |
| 4,877,744 | 10/1989 | Chang | 436/162 |
| 4,939,924 | 7/1990 | Johnson | 73/61.1 |

OTHER PUBLICATIONS

Dual Electrode Liquid Chromatography Detector for Thiols and Disulfides Laura A. Allison, Anal. Chem. 1983 Month Unavailable, 55–8–12.
Sample Processing Alters Glutathione and Cysteive Values in Blood. Betty J. Mills, Anal. Biochemistry, 184, 263–67 (1990) Month Unavailable.
Richie et al. "The Determination of Glutathione 1.1" Analytical Biochemistry, 163–9–15. (1987) Month Unavailable.
Allison, L.A. et al. "Dual Electrode Liquid . . . " Anal Chem 1983, 1983, Month Unavailable 55, 8–12.
Capillary Zone Electrophoretic Detection of Biological Thiols and Their S–Nitrosated Derivatives, Jonathan S. Stamler, Anal Chem. 1992 Month Unavailable, 64, 779–785.
The Determination of Glutathione Cyst(e)ine, and other Thiols and Disulfides . . . John P. Richie, Anal. Biochemistry 163, 9–15 (1987) Month Unavailable.

*Primary Examiner*—T. Tung
*Attorney, Agent, or Firm*—Ladas & Parry

[57] ABSTRACT

A method for detecting a nitrosothiol in an eluant from a chromatographic process including passing the eluant through a series of electrodes comprising an upstream working electrode and a downstream working electrode. The upstream working electrode is maintained at a potential adequate to reduce the nitrosothiol to a corresponding thiol. The downstream electrode is maintained at a potential to detect the corresponding thiol.

21 Claims, 8 Drawing Sheets

S - NITROSOTHIOLS

S-NITROSOHOMOCYSTEINE

FIG. 1(b)

S-NITROSOCYSTEINE

FIG. 1(a)

S-NITROSOGLUTATHIONE

METHODS FOR THE SEPARATION AND DETECTION OF NITROSOTHIOLS

FIELD OF INVENTION

The present invention relates to liquid chromatographic methods and apparatus. More particularly, the invention relates to methods and apparatus for the detection of nitrosothiols in an eluant from a chromatographic process. The methods and apparatus can be used for the analysis of nitrosothiols in human tissues and fluids for diagnostic purposes.

BACKGROUND OF THE INVENTION

Nitric oxide (NO) has recently been identified as an important biological regulator involved in a number of diverse physiological processes such as blood pressure regulation, central nervous system communications, and the immunological destruction of tumor cells and parasites. Altered NO production has been implicated in a number of disease states ranging from cardiovascular disease to impotency. Recent studies have demonstrated that many of the functions of NO are mediated through the formation of s-nitrosothiol compounds (RSNO). The biological activity of s-nitrosothiols has been reported to include the following:

Smooth Muscle Relaxation

EDRF

Penile erection

Lung function

Platelet Aggregation Inhibition

Immune Regulation

Tumoricidal, Bactericidal

Neurotransmission
  Memory formation
  Motor neuron development

Neutrophil Function Inhibition

Enzyme Regulation

Hexase Monosphate Shunt Activation

Guanylate Cyclase Activation

However, the role of RSNO in human disease has not yet been elucidated due to the lack of suitable analytical methods for their separation and identification in physiological samples. Previous reported methods are limited primarily by their lack of sensitivity.

For example, a previously known method for separating and detecting nitrosothiols uses high performance capillary electrophoresis (HPE) and requires the use of capillary zone electrophoresis with nitrosothiols being separated on the basis of their molecular weight and net charge. Stamler, et al (1992) *Analytical Chemistry* 64, 779–785. Although purportedly capable of detecting picomole quantities of S-nitrosothiols, the concentration detection limits of HPE are in the micromolar range. Thus, the current generation of commercial analytical systems using HPE is likely to be of limited usefulness for investigations at the cellular level. Similarly, with the exception of glutathione, which is present in micromolar to millimolar concentrations intracellularly, the physiologic concentrations of the other biologic thiols are at the limits of the sensitivity of HPE.

In view of the insufficiency of the previously known method, what has been needed is a simple and sensitive method for the separation and detection of nitrosothiols. In this respect, there is known a simple and sensitive method for the separation and detection of thiols and disulfide compounds using a high pressure liquid chromatography-dual electrochemical method (Richie, et al. (1987) *Anal. Biochem.* 163, 9–15). This method uses a dual electrochemical detector consisting of two AU/Hg thin-layer electrodes in series. At the upstream electrode, disulfides are reductively cleaved to thiols, and at the downstream electrode, the thiols are detected by an increase in current. Richie, et al. at page 10. This detector reaction is indirect and based on the oxidation of mercury in the presence of certain species such as thiols, as follows:

$$2RSH + Hg \rightarrow Hg(SR)_2 + 2H^+ + 2e^-$$

The detector may be poised at very low potential, typically +0.1 V vs. Ag/AgCl, in contrast to the +0.9 to 1.0 V potentials required for direct oxidation of thiol to the disulfide on, for example, a carbon surface. Allison, et al. (1983) *Anal. Chem* 55, 8–12. This approach has been refined for the therapeutic agent penicillamine by employing a mercury film on gold surface (eventually creating an amalgam). Allison et al. at page 8. This approach has been used to demonstrate sample detection limits of approximately $10^{-7}$M. Id.

Although the determination of thiols in biological tissues using the high pressure liquid chromatography-dual electrochemical techniques (Allison et al, supra; Mills et al., (1990) *Anal Biochem* 184, 263–267) has been practiced, the techniques were not applied for detection of nitrosothiols. Specifically, it has not been previously recognized that high pressure liquid chromatography with electrochemical detection could be used to separate and detect nitrosothiols.

SUMMARY OF THE INVENTION

It is an object of the invention to provide a sensitive method for the detection of nitrosothiols.

It is another object of the invention to separate and detect nitrosothiols from other components in a sample solution.

It is a further object of the invention to provide a method for reducing nitrosothiols to their corresponding thiols so that they can be readily detected.

In accordance with the above and other objects of the invention, there is provided a method for detecting a nitrosothiol in an eluant from a chromatographic column comprising passing the eluant through a series of electrodes comprising an upstream working electrode and a downstream working electrode. The upstream working electrode is maintained at a potential adequate to reduce said nitrosothiol to a corresponding thiol. The downstream electrode is maintained at a potential to detect said corresponding thiol. Since the nitrosothiol present in said eluant will usually be present along with one or more other compounds, the downstream electrode is maintained at a potential adequate to detect said corresponding thiol substantially without oxidation or reduction of said one or more other compounds.

In a preferred embodiment of the invention, each of the upstream and downstream electrodes comprises an amalgam of Hg on the surface of a metal, such as gold. The upstream working electrode is maintained at a potential of about −0.4 V. The downstream working electrode is maintained at a potential of about +0.15 V. These potentials are measured with respect to at least one reference electrode which, in a preferred embodiment, comprises Ag/AgCl.

BRIEF DESCRIPTION OF THE DRAWING

In the Drawing:

FIGS. 8(a)–(d) are graphs showing HPLC-DEC profiles of rat brain tissue extracts before and after addition of S-nitrosoglutathione;

DETAILED DESCRIPTION

Figure 1A:
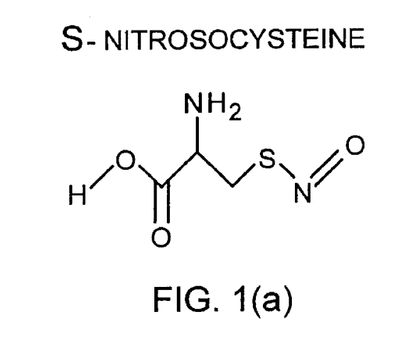
FIGS. 1(a)–(c) depict the respective chemical structures of three common s-nitrosothiols.
Figure 1B:
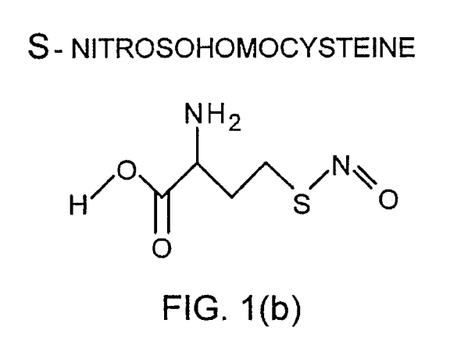
Figure 1C:
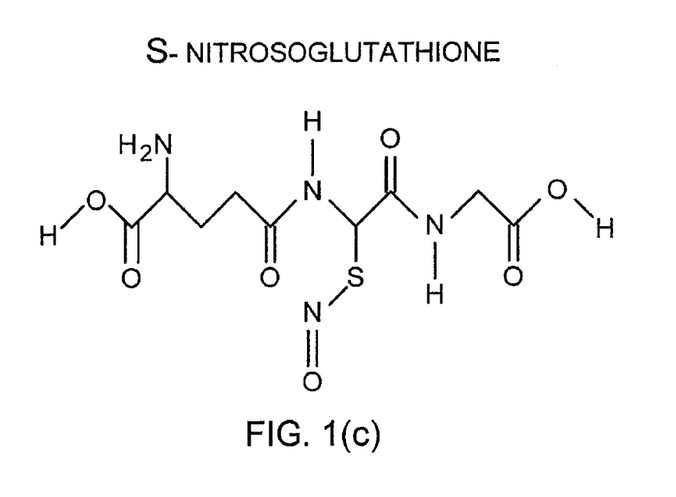

Three common s-nitrosothiols are shown in FIGS. 1(a)–(c). In a preferred embodiment of the invention, a biological sample suspected of containing, for example, one of the above nitrosothiols (RSNO) along with other compounds is first separated into its components by high performance liquid chromatography using known methods. For example, a sample to be tested may be introduced into a chromatography column packed with ion exchange resins in bed or powder form. The sample may be introduced as a dilute solution, with the solution comprising a mobile phase which is made to flow over the ion exchange resins which comprise a stationary phase. A pump may be used to cause the mobile phase to flow over the stationary phase. As the mobile phase moves past the stationary phase, repeated adsorption and desorption of the solute causes components of the solution to move at different rates producing an eluant from the chromatography column in which the components are separated and may be detected. The selection of suitable chromatography apparatus and ion exchange resins are known to those of skill in the art and will not be further described herein.

Figure 2:
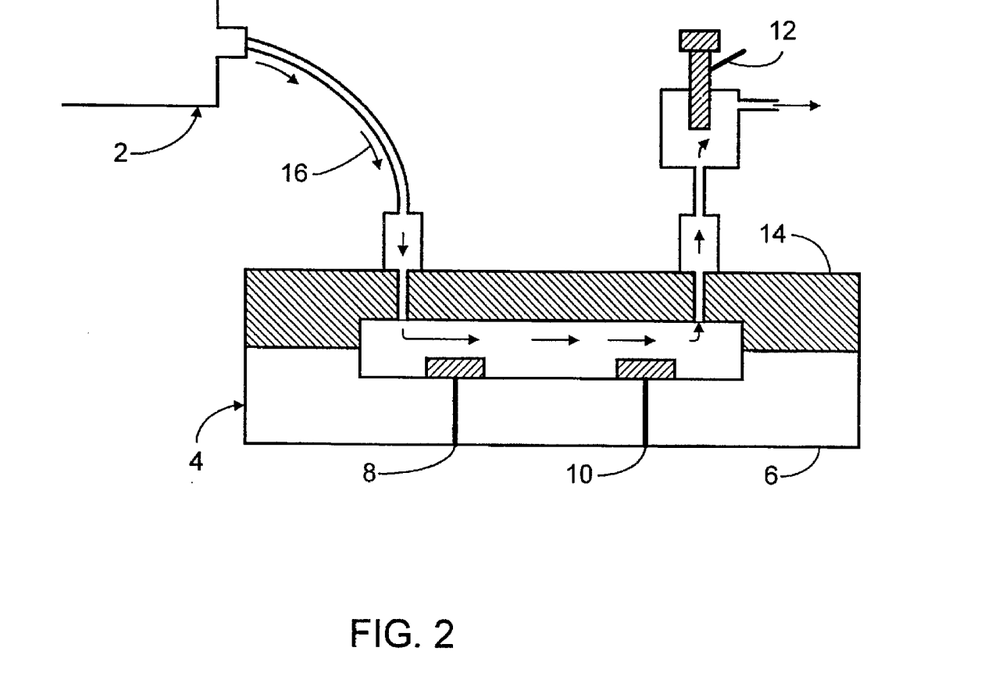
FIG. 2 shows a dual electrochemical detector cell for use in the separation and detection of nitrosothiols.

Referring to FIG. 2, detection of nitrosothiols in the eluant received from a chromatographic column 2 may be accomplished according to the invention by passing the eluant in the direction of arrow 16 through an electrochemical detection cell 4 comprising a working electrode block 6 having dual working thin layer electrodes 8 and 10. The electrodes can be arranged in a series configuration with the upstream working electrode 8 set at a potential of $\leq -0.4$ V to reduce the nitrosothiols in the eluant to their corresponding thiols. As discussed further below, the upstream working electrode should preferably be set at a potential of $\leq -0.4$ V to reduce RSNO to a corresponding thiol, and at a potential of $-1.0$ V to reduce both RSNO and RSSR to their corresponding thiols. The downstream working electrode 10 may be set at a potential of about $\geq 0.15$ V, preferably +0.15 V, for thiol detection.

Figure 3:
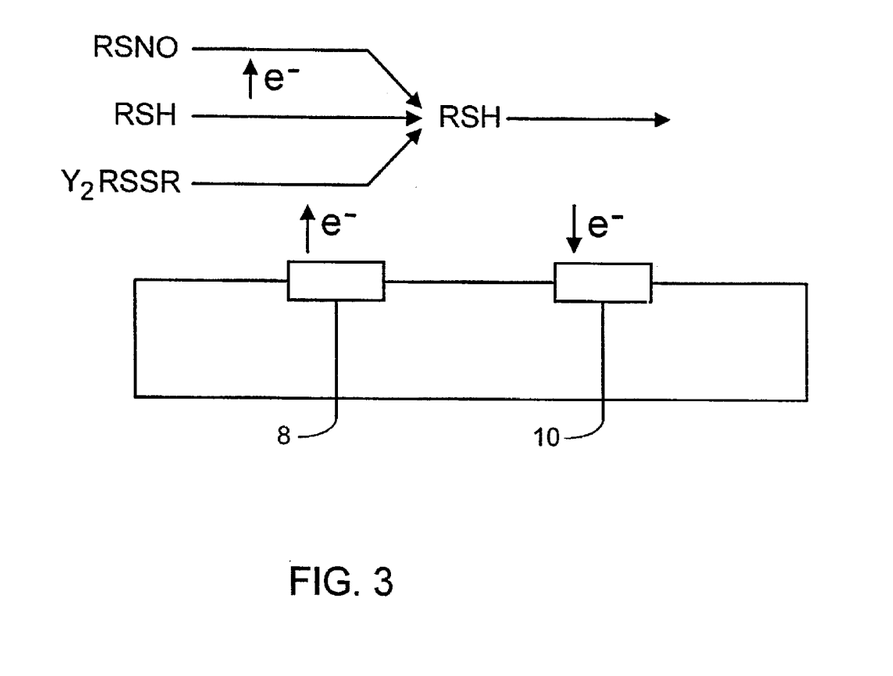
FIG. 3 is a diagrammatic exemplification of the electrochemical reactions occurring at respective upstream and downstream electrodes of the dual electrochemical detector cell of FIG. 2.
Figure 4:
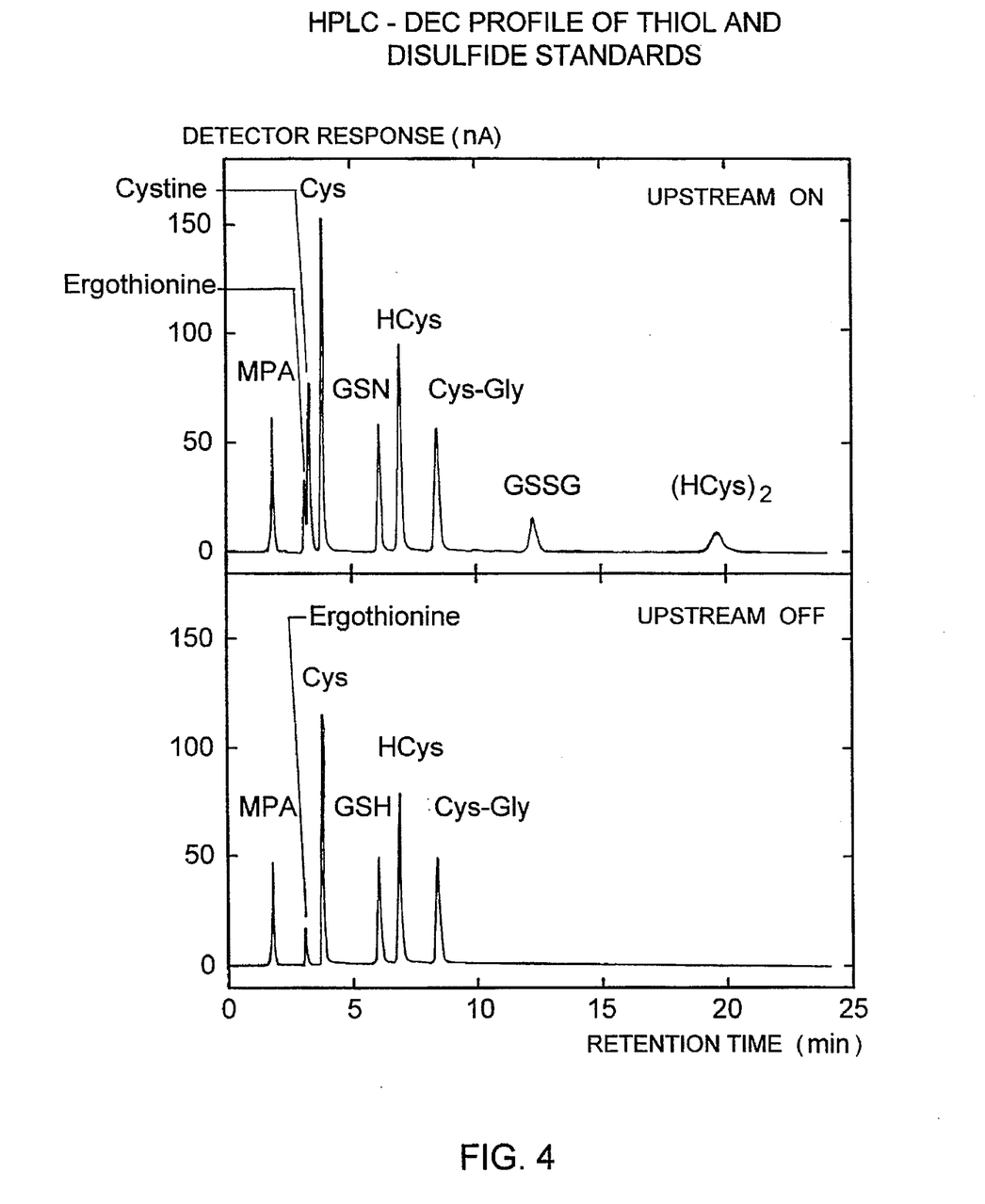
FIG. 4 is a graph comparing a HPLC-DEC profile for thiols and disulfides with the upstream electrode on and with the upstream electrode off.
Figure 6:
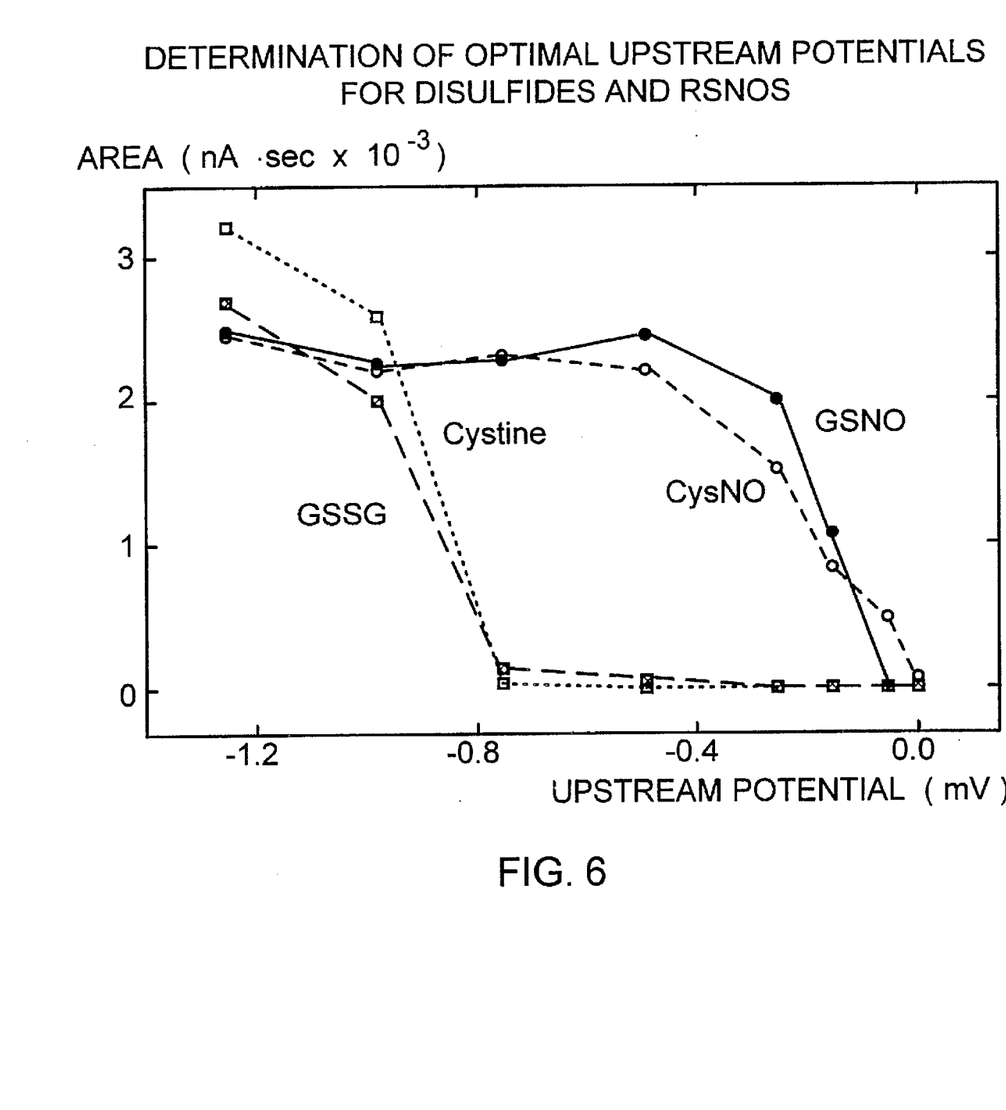
FIG. 6 is a graph showing the effect of upstream potential on detection of s-nitrosothiols and disulfides.

FIG. 3 shows diagrammatically the reduction and oxidation reactions that occur at the respective upstream and downstream electrodes 8 and 10. It is necessary to reduce the nitrosothiols to their corresponding thiols at the upstream electrode 8 because detection is performed at the downstream electrode on the free thiol only. When NO is bound to the thiol via the free SH group, the compound cannot be detected at the downstream electrode 10. Thus, the reduction reaction is a critical step in the methodology. Similarly, disulfides must be reduced at the upstream electrode 8 to enable detection of the corresponding thiols at the downstream electrode (see FIG. 4). FIG. 6 shows the effect of varying the upstream potential on reduction (and subsequent detection) of the disulfides and nitrosothiols. To detect disulfides, the upstream electrode 8 should be set at $\leq -1.0$ V whereas, to detect nitrosothiols, the upstream electrode should be set at $\leq -0.4$ V. Accordingly, both nitrosothiols and disulfides can be detected in the same run if the upstream electrode is set at $\leq -1.0$ V.

In addition to upstream and downstream working electrodes 8 and 10, the electrochemical detection cell 4 (FIG. 2) will preferably comprise a counter electrode 14 for the working electrodes 8 and 10 and a reference electrode 12. The reference electrode 12 will supply a stable reference potential against which other electrochemical responses at the working electrodes can be measured. The reference electrode 12, in a preferred embodiment of the invention comprises an Ag/AgCl reference electrode. (All potentials specified herein are vs. an Ag/AgCl reference electrode.)

In a preferred embodiment of the invention, both the upstream and downstream working electrodes 8 and 10 will comprise a metal base having a surface comprising a mercury film or a mercury amalgam. It is preferred that the surfaces of the downstream electrodes be Hg or an Hg amalgam so that the chemistry of the detector reaction occurs between thiol groups and the mercury surface. Other surfaces such as gold or glassy carbon do not react with thiols in comparable fashion. Thus, while the oxidation of thiols can occur with other electrode surfaces, the voltages required would be so high that the background interference would severely limit the sensitivity and utility. Although mercury amalgam is not required at the upstream electrode (the reduction of disulfides and RSNOs will occur at electrodes composed of other materials), mercury amalgam is preferred for practical reasons. Since, in a preferred embodiment, both electrodes are contained in the same cell block, it is significantly easier to resurface both electrodes at the same time using the same procedures. In turn, it would be difficult to use a different polishing procedure for each electrode, as would be necessary if they were made of different materials. The upstream and downstream electrodes are preferably polished to a mirror finish.

Because of the specific reaction of thiols with Hg, the voltage at which oxidation occurs is significantly lowered compared to other electrode surfaces. Indeed, at the voltages used in the present method, very few compounds other than thiols, disulfides and nitrosothiols are affected. Thus, the method is both highly selective as well as sensitive.

Gold is preferable as the base for the mercury amalgam because it is a good and convenient electrical conductor. However, other metals are also suitable.

The dual electrochemical cell 4 for use in the invention can be a commercially available detector which can provide dual thin-layer gold electrochemical cells for use with HPLC, such as dual electrochemical detection equipment available from Bioanalytical Systems, Inc. (Model LC-b 4B, BAS, W. Lafayette, Ind.). The composition of the mobile phase will primarily impact the retention times for the analytes. The mobile phase can be specifically designed to resolve all thiols, disulfides and nitrosothiols of interest. Although the composition of the counter electrode is not of great importance, stainless steel is preferred because of its chemical resistance and compatibility, ease of use and low cost.

The present methods can be used to detect in a single sample the major biological nitrosothiols including nitroso-adducts of glutathione, cysteine, homocysteine and N-acetylcysteine as well as thiols and disulfides including glutathione, disulfide, cysteine, cystine, homocysteine and homocystine. In principle, the subject method is applicable to all nitrosothiols, providing there are no stearic hindrances blocking the availability of the nitroso group. Sensitivity values for RSNO, thiols and disulfides are in the low nanomolar range. Indeed, nitrosothiols test could be detected to levels $\leq 10$ nmol/l. Thus, the present method is several orders of magnitude more sensitive for RSNO than any method previously reported. In addition, based upon the enhanced sensitivity, the present method is applicable for the measurement of RSNO in biological samples.

EXAMPLES

Example 1

Nitrosothiols (RSNO) including nitrosoglutathione (GSNO), nitrosocysteine (CYSNO) and nitrosohomocysteine (HCYSNO) are separated and analyzed by high performance liquid chromatography using dual electrochemical detection (HPLC-DEC). Chromatography is carried out using a Waters (Milford, Mass.) Model 510 pump, dual LC-4 B amperometric detector (BAS, West Lafayette, Ind.), and dual Au working thin layer electrodes with a Ag/AgCl reference electrode (BAS). The working electrodes are polished to a mirror finish and an Hg amalgam is prepared on the gold surface. The two electrodes are arranged in the series configuration with the upstream set at a potential of −0.4 V to reduce RSNO to its corresponding thiol and the downstream electrode at +0.15 V for thiol detection. A Rheodyne 7125 injector is used with a GL Sciences Intersil 5 μM ODS-2 250×4.6 mm column (Alltech, Deerfield, Ill.) and a Hitachi (Danbury, Conn.) D-2500 integrator for peak integration and data retrieval. In the chromatographic system, stainless steel is replaced with Peek components wherever possible to prevent metal interactions. Samples are run isocratically at a flow rate of 1 ml/min, using a mobile phase of 93.25% (v/V) 0.1M monochloroacetic acid/5% methanol/1.75% dimethylformamide (DMF)/2.25 mM heptanesulfonic acid (pH 2.8). The resultant profiles were quantified with external standards based on peak areas. Using these conditions, the following retention times are obtained for RSNO: 5.24 min for CYSNO, 17.7 min for HCYSNO and 16.8 min for GSNO. Thiols such as glutathione (6.09 min), Cysteine (2.79 min) and homocysteine (6.89 min) are also detected under these conditions. The upstream electrode must be set to −1.0 V in order to detect disulfides including cystine (3.29 min), glutathione disulfide (12.2 min) and homocystine (19.8 min).

Figure 5:
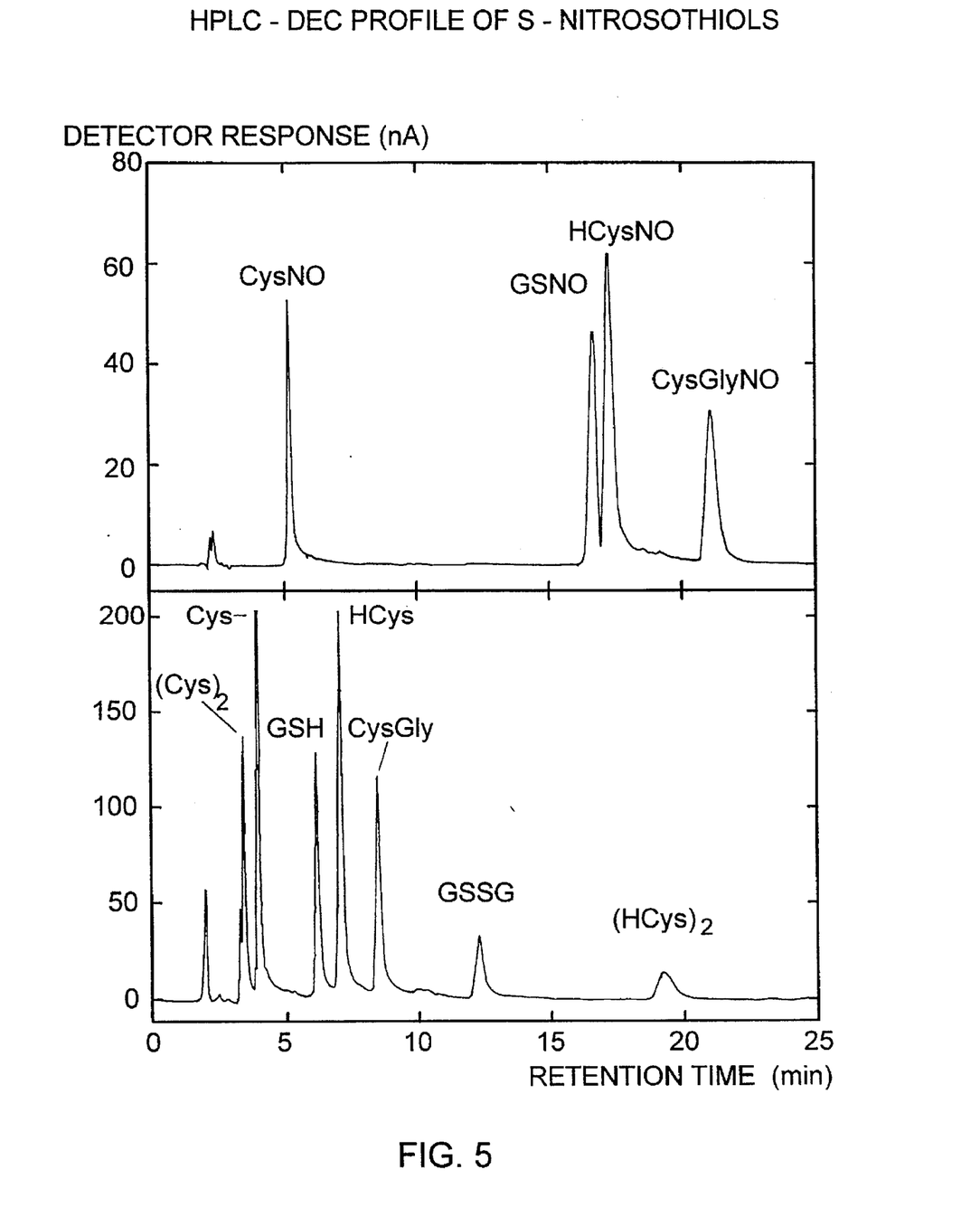
FIG. 5 is a graph showing a HPLC-DEC profile of biologically important s-nitrosothiols.

FIG. 5 is a graph showing the detection of nitrosothiols using the present method.

Example 2

Figure 7:
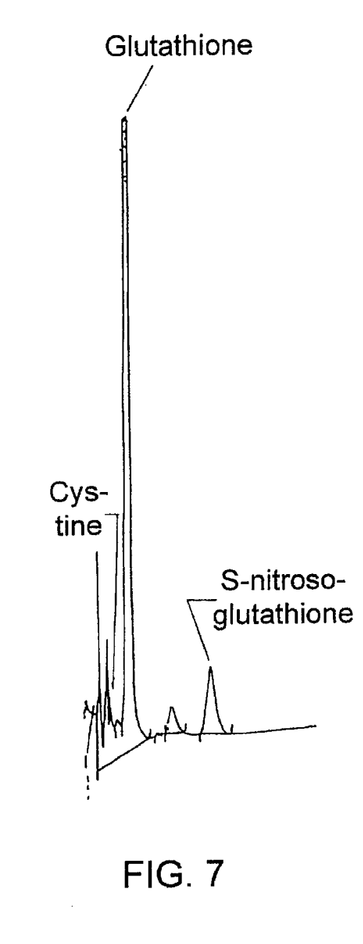
FIG. 7 is a graph showing a HPLC-DEC profile of human red cell extracts containing added S-nitrosoglutathione.
Figure 8A:
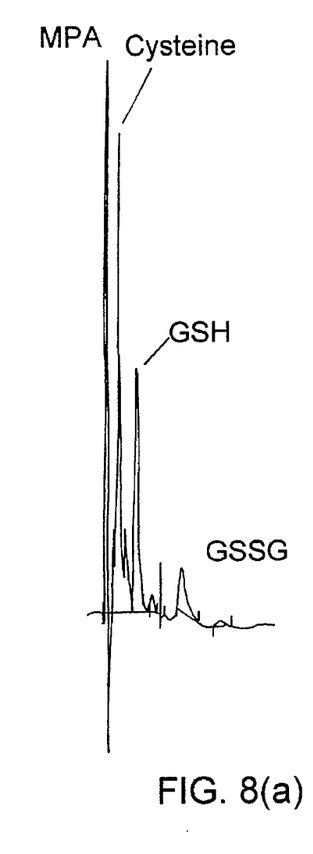
FIG. 8(a) shows rat brain tissue extract prior to GSNO addition.
Figure 8B:
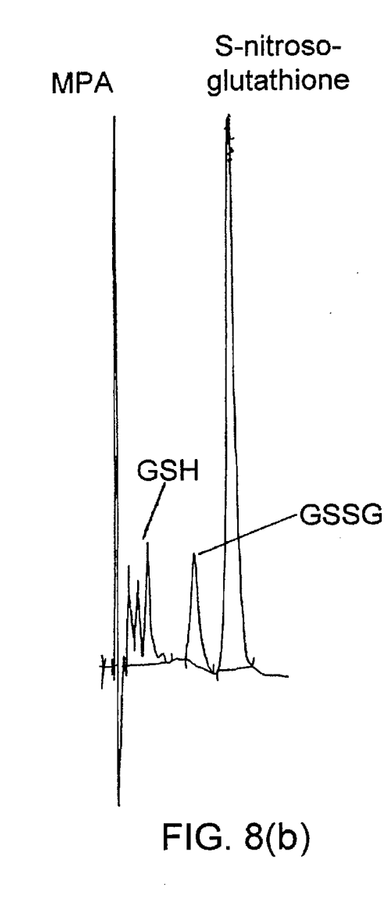
FIG. 8(b) shows rat brain tissue extract 0.25 minutes after GSNO addition.
Figure 8C:
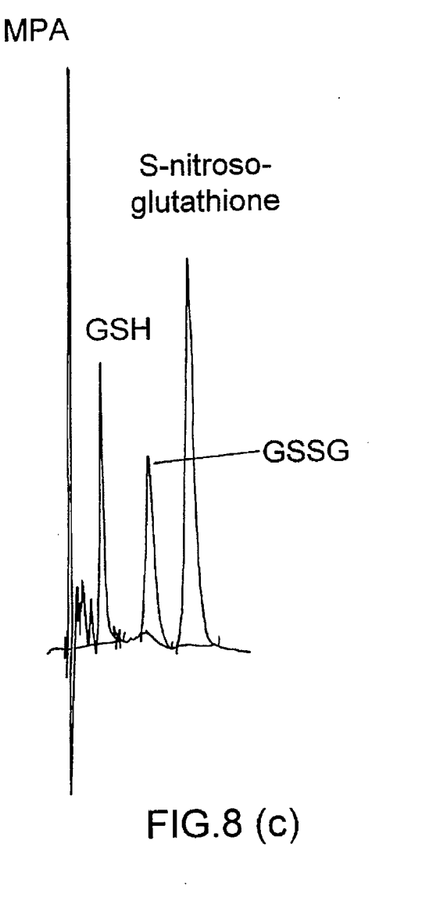
FIG. 8(c) shows rat brain tissue extract 1 hour after GSNO addition.
Figure 8D:
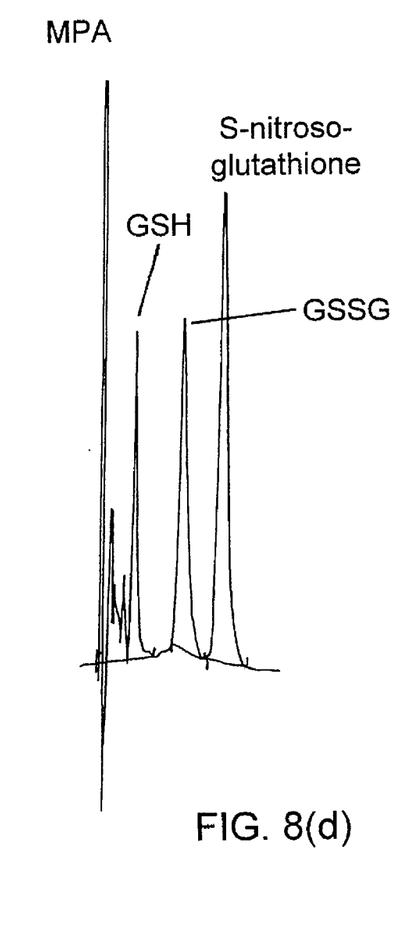
FIG. 8(d) shows rat brain tissue extract 2 hours after GSNO addition.

The present methods were used to measure the recovery of S-nitrosoglutathione added to human red cell extract. Fresh human blood was immediately centrifuged. A ⅕ (v/v) hemolysate was made with $H_2O$ and 200 μM S-nitrosoglutathione was added. The sample was processed with 1 vol. 5% metaphosphoric acid (MPA) prior to analysis on HPLC-DEC. The results are shown in FIG. 7.

Example 3

The present methods were used to measure the stability of S-nitrosoglutathione added to rat brain tissue extracts. Rat brain was homogenized (⅕, v/v) in saline and centrifuged. 200 μM S-nitrosoglutathione (GSNO) was added to the resulting supernatant. After incubation, samples were processed ½ (v/v) with 5% MPA and analyzed by HPLC-DEC. The results are shown in FIGS. 8(a–d).

Example 4

Figure 9A:
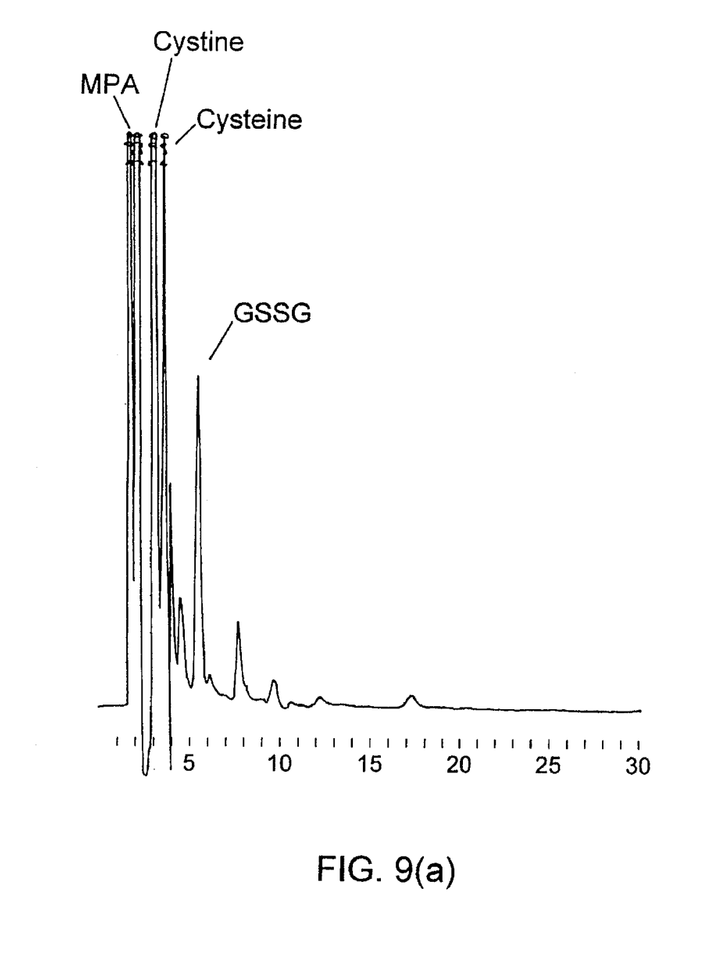
FIGS. 9(a) and (b) are graphs showing HPLC-DEC profiles of human plasma with and without addition of GSNO respectively.
Figure 9B:
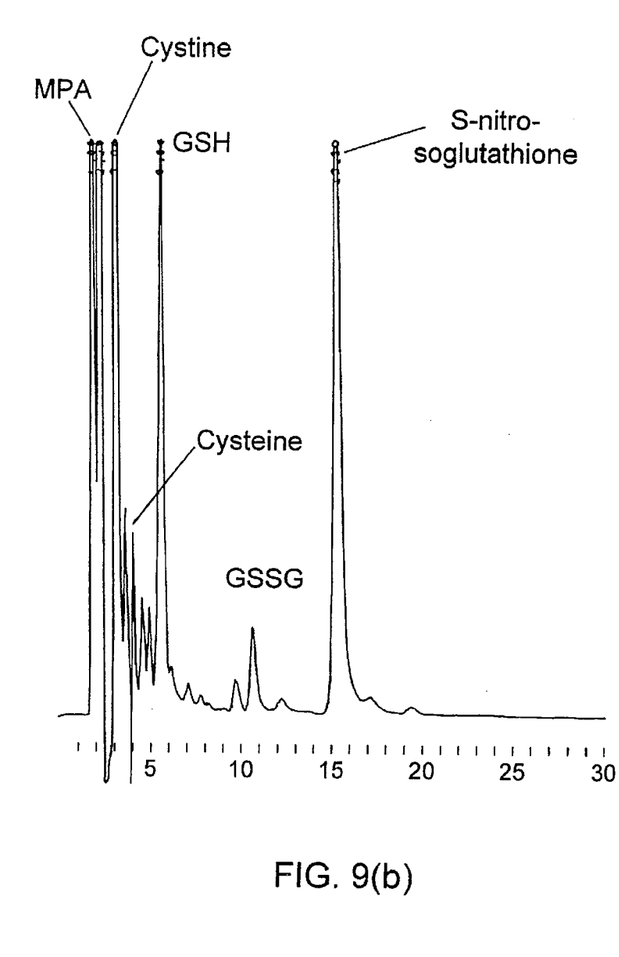

The present methods were used to measure the recovery of S-nitrosoglutathione added to human plasma. Freshly drawn blood was immediately centrifuged, plasma separated and process with the addition of 1 vol. 5% metaphosphoric acid (MPA). The results of an HPLC-DEC analysis on this control sample are shown in FIG. 9. The process was then repeated except that 200 μM S-nitrosoglutathione was added to plasma prior to processing with MPA. The results of an HPLC-DEC analysis of the resultant sample is provided in FIG. 10.

The present method fulfills a critical need in research on the biochemistry and physiology of NO and RSNO. Utilization of this method should provide important information on the role of these compounds in health and disease processes in humans. Applications include its use in the clinical evaluation of NO and RSNO status in patients as a diagnostic indicator of disease status. Applications also include the measurement of S-nitrosothiols in biological fluids, including measurement of the stability of S-nitrosothiols in such fluids and measurement of the recovery of S-nitrosothiols from such fluids.

Other advantages of the invention will become apparent to those skilled in the art and numerous modifications and adaptations will become evident which do not depart from the scope and fair meaning of the invention as described hereinabove and as defined by the following claims.

What is claimed is:

1. A method for detecting a nitrosothiol in an eluant comprising a) passing the eluant through a series of electrodes comprising an upstream working electrode and a downstream working electrode, the upstream working electrode being maintained at a potential adequate to reduce said nitrosothiol to a corresponding thiol, said downstream electrode being maintained at a potential to detect said corresponding thiol, and b) detecting said correspond thiol.

2. A method according to claim 1 wherein said nitrosothiol is present in said eluant along with at least one other compound, said at least one other compound being separated from the nitrosothiol in the eluant such that the nitrosothiol and the at least one other compound pass through the series of electrodes at different times.

3. A method according to claim 2 wherein at least the downstream working electrode comprises an amalgam of Hg.

4. A method according to claim 3 wherein the upstream working electrode is maintained at a potential of about −0.4 to −1.0 V.

5. A method according to claim 4 wherein the downstream working electrode is maintained at a potential of about at least +0.15 V.

6. A method according to claim 5 wherein the potential of each of the upstream and downstream electrodes is measured with respect to at least one reference electrode.

7. A method according to claim 6 wherein each of the upstream and downstream working electrodes comprises a noble metal base having a surface comprising mercury.

8. A method according to claim 7 wherein the reference electrode comprises Ag/AgCl.

9. A method according to claim 5 wherein the nitrosothiol is selected from the group consisting of nitrosoglutathione (GSNO), nitrosocysteine (CYSNO) and nitrosohomocysteine (HCYSNO).

10. A method according to claim 2 wherein said at least one other compound incudes a disulfide, and the upstream electrode is set at a potential of $\leq -1.0$ V to reduce both the nitrosothiol and the disulfide to their respective corresponding thiols, said step b) comprising detecting the respective corresponding thiols.

11. A method for reducing a nitrosothiol (RSNO) to a corresponding thiol (RSH), said method comprising passing a solvent containing said nitrosothiol through an electrochemical cell comprising a working electrode maintained at a potential adequate to reduce said nitrosothiol to said corresponding thiol.

12. A method according to claim 11 wherein the working electrode comprises a mercury amalgam.

13. A method according to claim 12 wherein the electrochemical cell further comprises a counter electrode and a reference electrode.

14. A method according to claim 13 wherein the working electrode is maintained at a potential of about −0.4 V.

15. A method of liquid chromatographic analysis to separate and detect nitrosothiols from other components in a sample solution, said method comprising a) flowing the solution through chromatographic separation means to separate the nitrosothiols from the other components upon elution thereof;

b) passing an effluent from said chromatographic means through a first flow-through cell wherein an electric potential is applied to an upstream working electrode to reduce the nitrosothiols to their corresponding thiols; and c) detecting the corresponding thiols formed in step (b) by passing the effluent through a second flow-through cell wherein an electrical potential is applied to a downstream working electrode.

16. A method according to claim 15 wherein each of the upstream and downstream electrodes comprises a mercury amalgam.

17. A method according to claim 16 wherein a potential of between 0.4 V and −1.0 V is applied to the upstream electrode and a potential of at least +0.15 V is applied to the downstream electrode.

18. A method according to claim 17 wherein each of said first and second flow-through cells also comprises a reference electrode and a counter electrode.

19. A method according to claim 18 wherein the sample solution is caused to flow through said chromatographic separation means isocratically at a flow rate of about 1 ml/min.

20. A method according to claim 15 wherein said other components include a disulfide, said disulfide being separated from the nitrosothiols in step a) whereby the nitrosothiols and the disulfide pass through the first flow-through cell in step b) at different times, and wherein the upstream electrode is set at a potential of $\leq -1.0$ V whereby the upstream electrode reduces both the nitrosothiols and the disulfide to their respective corresponding thiols, said step c) comprising detecting the respective corresponding thiols.

21. A method as claimed in claim 15, wherein the method is used to detect nitrosothiols in a biological fluid or tissue extract of a patient to be tested, said method comprising preparing the sample solution flowing through the chromatographic separation means in step a) so that it contains said biological fluid or tissue extract.

* * * * *